(12) United States Patent
Dietz et al.

(10) Patent No.: US 7,339,011 B2
(45) Date of Patent: Mar. 4, 2008

(54) AMPHIPHILIC ORGANOPOLYSILOXANES HAVING POLYESTER GROUPS AND USE THEREOF AS EMULSIFIERS OF DISPERSING AGENTS

(75) Inventors: Thomas Dietz, Richmond, VA (US); Sascha Oestreich, Essen (DE)

(73) Assignee: Goldschmidt GmbH, Essen (DE)

( * ) Notice: Subject to any disclaimer, the term of this patent is extended or adjusted under 35 U.S.C. 154(b) by 145 days.

(21) Appl. No.: 11/400,979

(22) Filed: Apr. 10, 2006

(65) Prior Publication Data

US 2006/0183847 A1    Aug. 17, 2006

Related U.S. Application Data

(62) Division of application No. 10/664,713, filed on Sep. 18, 2003, now Pat. No. 7,084,215.

(30) Foreign Application Priority Data

Sep. 21, 2002    (DE)    ................ 102 43 992

(51) Int. Cl.
*C08G 77/445* (2006.01)
(52) U.S. Cl. ...................... 525/474; 525/446
(58) Field of Classification Search ................ 525/474, 525/446
See application file for complete search history.

(56) References Cited

U.S. PATENT DOCUMENTS

| | | | |
|---|---|---|---|
| 4,988,504 A | 1/1991 | Zotto et al. | |
| 5,051,489 A | 9/1991 | Zotto et al. | |
| 5,385,730 A | 1/1995 | Ichinohe | |
| 5,411,729 A | 5/1995 | O'Lenick, Jr. | |
| 5,475,125 A | 12/1995 | O'Lenick | |

FOREIGN PATENT DOCUMENTS

| | | |
|---|---|---|
| EP | 0 176 844 B1 | 12/1991 |
| EP | 0 407 089 B1 | 3/1993 |
| EP | 0 819 426 A2 | 1/1998 |
| JP | 04149232 A | 5/1992 |

*Primary Examiner*—Kuo-Liang Peng
(74) *Attorney, Agent, or Firm*—Scully, Scott, Murphy & Presser, P.C.

(57) ABSTRACT

The invention relates to organopolysiloxane copolymers comprising, on average, at least one polyester group bonded to the siloxane via a spacer and, on average, at least one hydrophilic group bonded to the siloxane via a spacer, of the general formula (I):

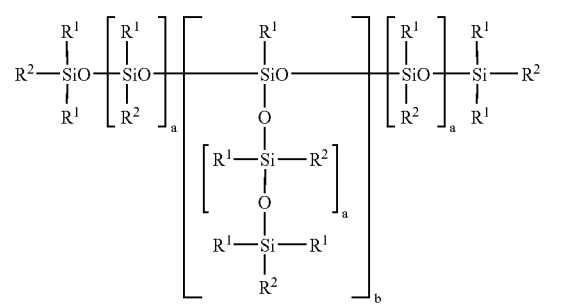

(I)

7 Claims, No Drawings

AMPHIPHILIC ORGANOPOLYSILOXANES HAVING POLYESTER GROUPS AND USE THEREOF AS EMULSIFIERS OF DISPERSING AGENTS

RELATED APPLICATIONS

This application is a divisional of U.S. patent application Ser. No. 10/664,713, filed Sep. 18, 2003 now U.S. Pat. No. 7,084,215.

FIELD OF THE INVENTION

The present invention relates to amphiphilic organopolysiloxanes having polyester groups and to the use thereof as emulsifiers or as dispersing agents.

BACKGROUND OF THE INVENTION

Organopolysiloxanes having polyester groups have been known for a long time. For example, U.S. Pat. No. 5,051,489 describes hydrophobic silicone polyester waxes that are obtained by esterification of the silanol groups of siloxanediols with dicarboxylic acids and fatty acids. These waxes are polyesters with a blockwise structure of dialcohols and dicarboxylic acids in which the polysiloxane takes on the function of the dialcohol.

U.S. Pat. No. 5,385,730 discloses mixtures consisting of a low-viscosity silicone oil and a polyester-radical-carrying polysiloxane with a block structure whose polyester radicals are obtained by lactone ring-opening. As well as the polyester radicals, these polysiloxanes can also carry long-chain alkyl radicals. These polysiloxanes are hydrophobic polysiloxanes that can be used as polishes.

Japanese Patent No. B-3046340 describes polyesters that are obtained by the reaction of terminal aliphatic hydroxyl-group-containing siloxanediols and dicarboxylic acids, such as adipic acid, and subsequent reaction with monocarboxylic acids, e.g., also hydroxystearic acid. The silicone polyesters are recommended for use in cosmetics.

U.S. Pat. No. 5,411,729 describes, inter alia, silicone polyesters which are obtained by reacting siloxanes carrying lateral or terminal polyether radicals having free OH groups with dicarboxylic acids and polyhydroxy compounds, such as glycerol, and optionally with a monofunctional carboxylic acid. The compounds are used as conditioning agents for hair. U.S. Pat. No. 5,475,125 discloses amphiphilic silicone polyesters that are obtained by reacting a comb-like polyethersiloxane having free OH groups with a dicarboxylic acid and a fatty alcohol ethoxylate. These amphiphilic silicone polyesters are recommended as emulsifiers for silicone oil-in-water emulsions.

From the description of the prior art it is clear that silicone polyesters of varying structure are known.

It is possible to differentiate between two basic types of polyester. Firstly those which are obtained by polycondensation of polyalcohols with dicarboxylic acids, and those which are obtained by self-condensation of hydroxy-functional carboxylic acids or by ring-opening reaction of corresponding lactones.

The first-mentioned type has a block structure if the polyalcohol is a diol. Here, the polysiloxane can take on the function of the diol, as described in U.S. Pat. No. 5,051,489 or Japanese Patent No. B-3046340. The siloxanediol can carry silanol-like OH groups, which leads to readily hydrolyzable Si—O—C bonds, or hydroxyalkyl groups, which produce hydrolysis-resistant Si—C bonds.

However, the siloxane can also carry more than 2 OH groups, as describe in U.S. Pat. No. 5,475,125. A disadvantage of the silicone polyesters prepared in this way is that the dicarboxylic acid used can act as a bridge between two silicone polyethers and triggers crosslinking reactions which are difficult to control and which may lead to complete gelation of the product.

U.S. Pat. No. 5,411,729 also discloses silicone polyesters which, as well as the polyhydroxy-functional siloxane, additionally contain an organic polyhydroxy compound as a building block. However, in this case too, crosslinking reactions are to be expected.

Silicone polyesters can be prepared in a more controlled manner by ring-opening reactions of lactones with hydroxy-functional siloxanes, see, for example, U.S. Pat. No. 5,385,730. In this way, crosslinking reactions can be completely avoided.

In principle, polyester siloxanes can be divided into amphiphilic and nonamphiphilic types. Siloxanes, which carry only polyester radicals, are usually hydrophobic and do not exhibit interface activity between a hydrophilic and a hydrophobic phase. Polyester siloxanes that also carry hydrophilic groups, such as, for example, polyether radicals are, by contrast, interface-active and can be used, for example, as emulsifiers. This is disclosed, for example, in U.S. Pat. Nos. 5,411,729 and 5,475,125.

The use of amphiphilically modified polysiloxanes, in particular polyether-modified polysiloxanes, as emulsifiers and dispersing agents has been known for a long time. The use of interface-active silicone polyethers in emulsifier systems is described in detail, for example, in U.S. Pat. No. 4,988,504. Polysiloxane compounds are proposed which consist of a) units of the formula $R_2SiO_{2/2}$, wherein R=hydrogen or a substituted or unsubstituted hydrocarbon radical having 1 to 12 carbon atoms, b) units of the formula $RR^1SiO_{2/2}$, wherein $R^1$=polyalkylene ether of the formula —$R^3{}_a$—$(OR^2)_n$—$OR^4$, in which $R^2$=—$CH_2CH_2$—, $R^3$=substituted or unsubstituted alkylene group having 1 to 20 carbon atoms, $R^4$=R, n has a value from 5 to 20, and a is 0 or 1, and c) end members of the siloxane chain, where the molecular weight of component a) should be about 25,000 to 35,000.

These emulsifiers with lateral polyoxyalkylene groups should bring about improved properties for antiperspirant sticks with regard to stability and low wax content.

European Patent B-0 407 089 relates to a transparent water-in-silicone oil emulsion, suitable for external application to mammallain skin or hair, comprising, in addition to water:

i. 1 to 50% by weight of a volatile polydimethylsiloxane;

ii. 0.1 to 20% by weight of a silicone surfactant ingredient comprising a polymer of dimethylpolysiloxane with polyoxyethylene and/or polyoxypropylene sidechains with a molecular weight of from 10,000 to 50,000 and the structural formula:

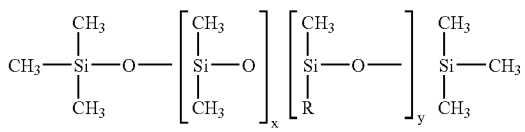

in which
R = —H or
—[CH$_2$CH$_2$O]$_a$[CH$_2$CHO]$_b$H,
         |
         CH$_3$ a has a value from 9 to 115,
b has a value from 0 to 50,
x has a value from 133 to 673, and
y has a value from 25 to 0.25; and iii. 1 to 50% by weight of a transparency-imparting agent, which is at least one polyhydric alcohol.

European Patent B-0 176 844 discloses the use of polysiloxanes with polyether and long-chain alkyl radicals added on in a comb-like manner as emulsifiers for the preparation of W/O emulsions, the oily phase of which consists of silicone oil, or comprises this. European Patent A-0 819 426 describes the use of terminally modified polyethersiloxanes as emulsifiers in W/O emulsions.

The disadvantage of prior art polyether-modified polysiloxanes described here is, however, that when the polyether-moified polysiloxanes are used as emulsifiers in W/O emulsions, undesirably high emulsion viscosities, especially in the case of emulsions with a high water phase content, are achieved.

SUMMARY OF THE INVENTION

An object of the present invention is therefore to provide emulsifiers for cosmetic W/O emulsions that have a low viscosity.

According to the present invention, this object is achieved by the use of organopolysiloxane copolymers comprising, on average, at least one polyester group bonded to the siloxane via a spacer and, on average, at least one hydrophilic group bonded to the siloxane via a spacer.

The present invention therefore provides organopolysiloxane copolymers comprising, on average, at least one polyester group bonded to the siloxane via a spacer and, on average, at least one hydrophilic group bonded to the siloxane via a spacer, of the general formula (I):

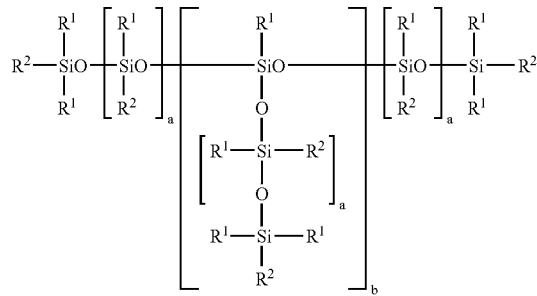

in which
$R^1$ are identical or different and are alkyl radicals having 1 to 30 carbon atoms or phenyl radicals,
$R^2$ independently of one another are $R^1$, -A-$R^3$ or —B—$R^4$ in which
-A- is a divalent alkyleneoxy group having 3 to 24 carbon atoms which is optionally branched and/or can contain double bonds, and/or is a divalent polyoxyalkylene group of the general average formula —$R^5$—(C$_2$H$_4$O)$_q$—(C$_3$H$_6$O)$_r$—(C$_4$H$_8$O)$_s$— in which
q=1 to 100,
r=0 to 100,
s=0 to 100,
$R^5$ is a divalent alkyleneoxy group having 1 to 24 carbon atoms which is optionally branched and/or can contain double bonds,
$R^3$ is a polyester radical of the general formula

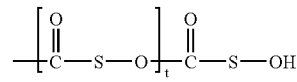

in which
t is integers in the range from 1 to 10, and [—(O=C)—S—O—] is the fragment of a corresponding hydroxycarboxylic acid HO—(O=C)—S—OH, in which
—S— is an optionally branched and/or double-bond-containing alkylene radical having 5 to 30 carbon atoms, with the proviso that at least 5 carbon atoms are between the carboxyl group [HO—C(O)—] and the hydroxyl group [—OH];
—B— acts as a spacer between siloxane backbone and the radical $R^4$ and is of a type known from the prior art for hydrophilically modified siloxanes,
$R^4$ is a hydrophilic radical of the general average formula —$R^6$—(C$_2$H$_4$O)$_q$—(C$_3$H$_6$O)$_r$—(C$_4$H$_8$O)$_s$—$R^7$ in which q=1 to 100,
r=0 to 100,
s=0 to 100,
$R^6$ is a divalent alkylene or alkyleneoxy group having 1 to 24 carbon atoms which is optionally branched and/or can contain double bonds;
$R^7$ is a hydrogen atom, alkyl or acyl radical having 1 to 20 carbon atoms, or
$R^4$ is a polyhydroxyorganyl radical, in particular a glycerol, polyglycerol, sugar or sugar derivative radical, a polyvinyl alcohol radical, a carboxylate, sulfate or phosphate radical, an ammonium radical or an amphoteric betaine or amphoglycinate radical,
a has a value from 1 to 1000, preferably 5 to 500, in particular 10 to 150, and
b has a value from 0 to 10, preferably b is <2, with the proviso that, on statistical average, at least in each case one radical $R^2$=-A-$R^3$ and $R^2$=—B—$R^4$ is present, or in the case where no radical —B—$R^4$ is present, at least one radical $R^2$=-A-$R^3$ is present in which -A- is a divalent polyoxyalkylene group of the above-described general average formula —$R^5$—(C$_2$H$_4$O)$_q$—(C$_3$H$_6$O)$_r$—(C$_4$H$_8$O)$_s$—.

A preferred embodiment of the present invention is organopolysiloxane copolymers of the general formula (I) in which the fragment [—(O=C)—S—O—]$_t$ corresponds to the radical of 12-hydroxystearic acid or of ricinoleic acid and t is between 2 and 5.

A further preferred embodiment of the present invention is organopolysiloxane copolymers of the general formula (I) in which the hydrophilic radical is selected from the group of polyethers.

The present invention further provides for the use of the polysiloxane copolymers of the general formula (I) as emulsifiers, optionally with co-use of further emulsifiers, for the preparation of low-viscosity W/O emulsions with a high content of disperse phase.

The present application further provides processes for the preparation of the compounds according to the present invention, which comprise adding on the polyester radicals either by hydrosilylation of polyesters carrying double bonds to polyhydrogensiloxanes, or by esterification of OH-functional polysiloxanes with polyesters carrying free carboxyl groups, and the hydrophilic radicals by processes known from the prior art to the polysiloxane. The spacers (B) are the radicals known from the prior art, such as $C_{1-24}$alkylene radicals, which may optionally be branched, and may optionally contain multiple bonds or heteroatoms, such as, in particular, oxygen atoms, and/or functional groups, such as, in particular, hydroxyl groups.

DETAILED DESCRIPTION OF THE INVENTION

As stated above, the present invention provides amphiphilic organopolysiloxanes having polyester groups that are useful as emulsifiers or dispersing agents. The inventive amphiphilic polysiloxanes are organopolysiloxane copolymers comprising, on average, at least one polyester group bonded to the siloxane via a spacer and, on average, at least one hydrophilic group bonded to the siloxane via a spacer, of the general formula (I):

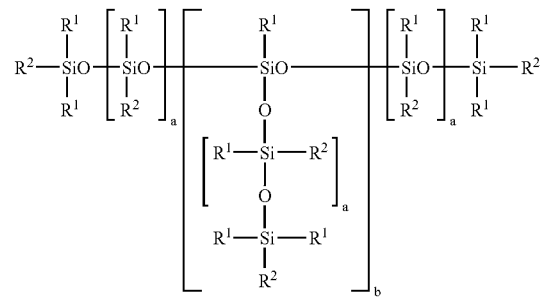

(I)

in which the variables $R^1$, $R^2$, a and b are as defined above.

The compounds of the general formula (I) are used in amounts of from about 0.5 to about 4% by weight, based on the total formulation, for the preparation of aqueous dispersions and emulsions, in particular for the preparation of W/O emulsions for cosmetic purposes, where the formulation constituents known for these fields of application, such as oil components, fats and waxes, polyols, active ingredients, such as vitamins, fruit acids and amino acids, such as creatine, perfume oils, dyes, pigments, UV filters, electrolytes, are co-used in the customary amounts.

Examples of compounds according to the present invention are:

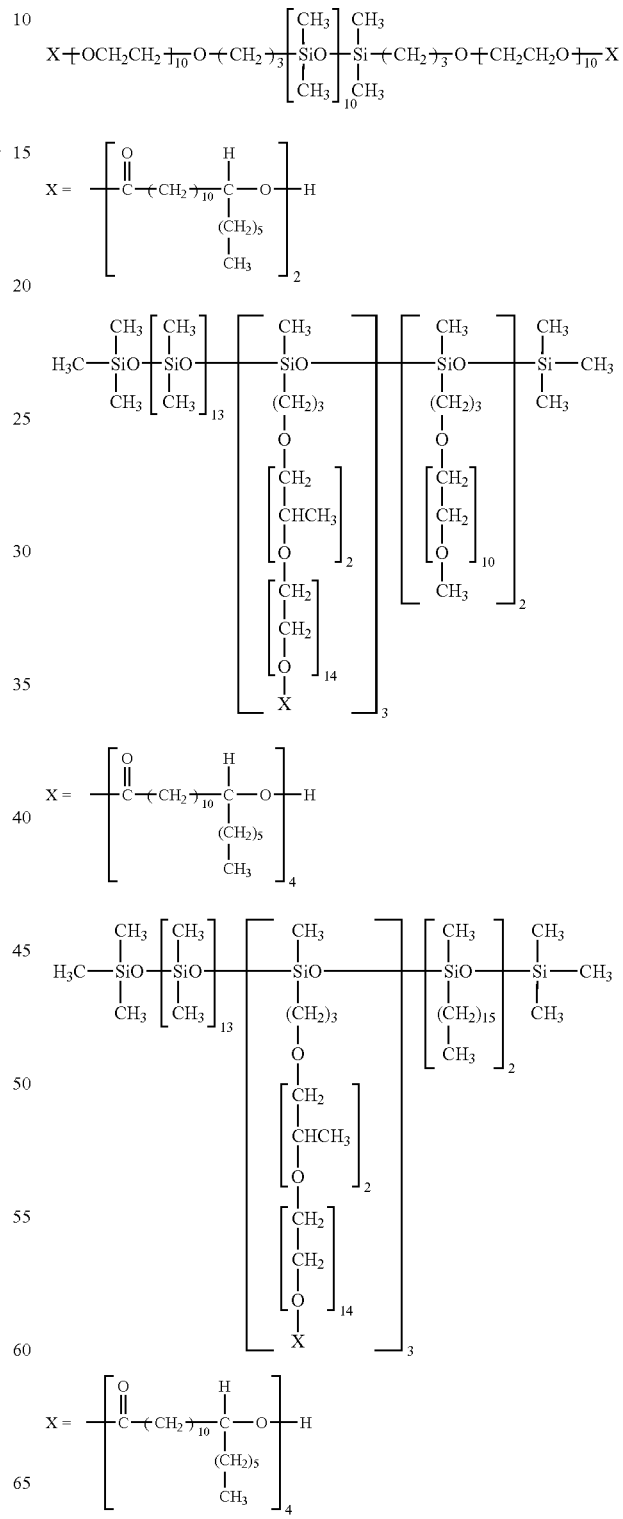

-continued

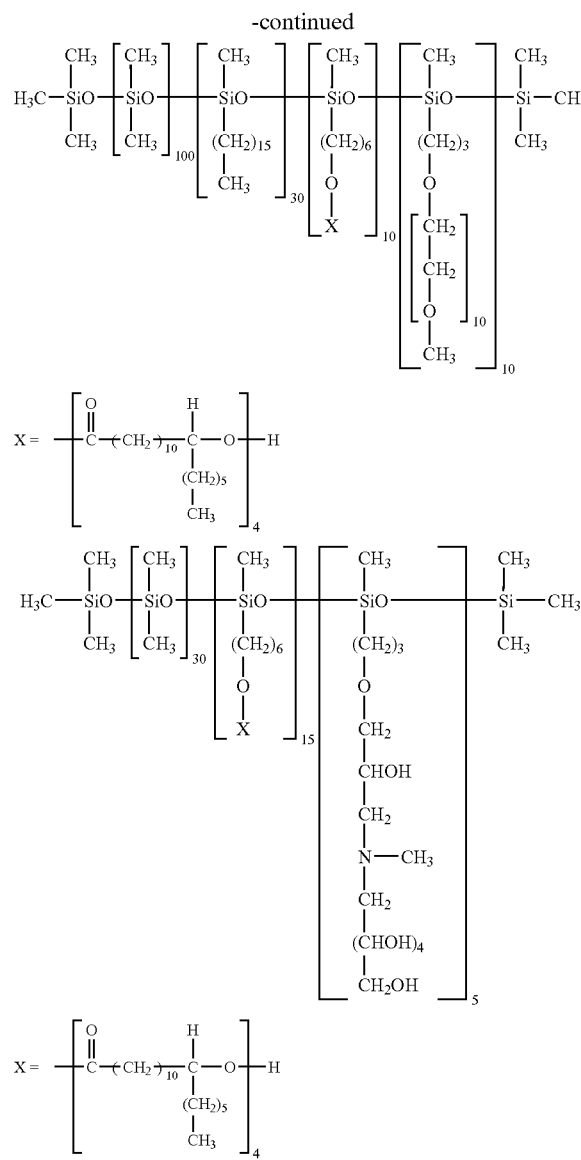

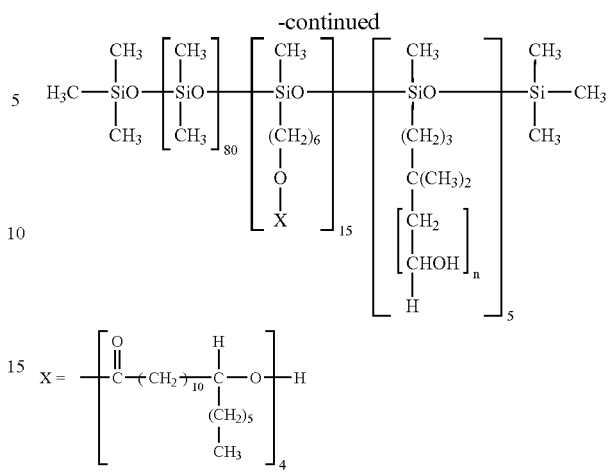

The compounds of formula (I) are prepared by adding on the polyester radicals either by hydrosilylation of polyesters carrying double bonds to polyhydrogensiloxanes, or by esterification of OH-functional polysiloxanes with polyesters carrying free carboxyl groups, and the hydrophilic radicals.

The examples below illustrate the present invention.

EXAMPLE 1

71.8 g of polyhydroxystearic acid (n=2, acid number=93.7 mg of KOH/g) were melted, homogenized and, together with 112.2 g of a doubly terminally modified polyether-siloxane (siloxane chain length N=10), molecular weight of the polyether (100% polyethylene glycol)=600 g/mol, OH number of the polyether-siloxane: 60 mg of KOH/g) and 120 g of toluene, were transferred to a 500 ml three-necked flask fitted with water separator, stirrer and thermometer. 0.55 g of methanesulfonic acid were added and the mixture was heated at 125° C. for 6 h with siring. The solvent was then removed on a rotary evaporator at 80° to 100° C. This gave a clear, brownish liquid. The conversion, determined by means of the final value of the acid number, was about 99%.

EXAMPLES 2 TO 4

TABLE 1

Experimental details for examples 2 to 4

| Example No. | Polyether-siloxane: Siloxane chain length N, Molecular weight of polyether MW [g/mol], OH number of polyethersiloxane [mg of KOH/g] | Initial wt of polyether-siloxane [g] | Initial wt of polyhydroxy-stearic acid [g] | Initial wt of methane-sulfonic acid [g] | Initial wt of toluene [g] |
|---|---|---|---|---|---|
| 2 | N = 10, MW = 400, OH number = 80 | 98.2 | 93.5 | 0.58 | 120 |
| 3 | N = 20, MW = 400, OH number = 59 | 114.1 | 80.1 | 0.58 | 120 |
| 4 | N = 80, MW = 400, OH number = 93.7 | 154.3 | 36.7 | 0.57 | 120 |

Applications Section:

EXAMPLE 5

| Phase | | Emulsion No. (Ingredient data in %) | | | | | | | | |
|---|---|---|---|---|---|---|---|---|---|---|
| | | 1 | 2 | 3 | 4 | 5 | 6 | 7 | 8 | 9 |
| A | Emulsifier from example 2 | — | 2 | — | 1.5 | 1.5 | — | — | — | — |
| | Emulsifier from example 3 | 2 | — | 2 | — | — | 1.5 | 1.5 | — | — |
| | Cetyl Dimethicone Copolyol (ABIL EM 90) | — | — | — | — | — | — | — | 2 | 2 |
| | Diisostearoyl Polyglyceryl-3 Dimer Dilinoleate (ISOLAN PDI) | — | — | — | 0.5 | 0.5 | 0.5 | 0.5 | — | — |
| | Microcrys-talline Wax | — | — | — | — | — | — | 0.25 | — | — |
| | Castor Wax | — | — | — | — | — | — | 0.25 | — | — |
| | Mineral Oil | — | 23 | 23 | 23 | — | — | 8 | 23 | 7.6 |
| | Ethylhexyl Stearate | 23 | — | — | — | 23 | 23 | 8 | — | 7.7 |
| | Caprylic/Capric Triglyceride | — | — | — | — | — | — | 8 | — | 7.7 |
| B | Glycerol | 2.45 | 2.45 | 2.45 | 2.45 | 2.45 | 2.45 | 3.35 | 2.45 | 2.45 |
| | Bronopol | 0.05 | 0.05 | 0.05 | 0.05 | 0.05 | 0.05 | 0.05 | 0.05 | 0.05 |
| | Magnesium Sulfate Heptahydrate | 0.5 | 0.5 | 0.5 | 0.5 | 0.5 | 0.5 | 0.5 | 0.5 | 0.5 |
| | Water | 72 | 72 | 72 | 72 | 72 | 72 | 68 | 72 | 72 |
| | Emulsion viscosity [Pas] after 2 days at room temperature (V1) and after 2 months at room temperature (V2) | V1 = 9 V1 = 7 | V1 = 6 V2 = 6 | V1 = 10 V2 = 7 | V1 = 11 V2 = 10 | V1 = 8 V2 = 7 | V1 = 8 V2 = 9 | V1 = 12 V2 = 13 | V1 = 36 V2 = 22 | V1 = 52 V2 = 28 |

The emulsions were prepared by adding the components of phase B to the components of phase A with stirring and then homogenizing the mixture for 1 min. with a hand rotor-stator mixer.

In the case of emulsion 7, the components of phase A have to be heated to about 80° C. so that the wax-like components (microcrystalline wax and castor wax) are molten. The oil phase can then be cooled again to room temperature and the procedure described above was followed.

Emulsions 8 and 9 are comparison emulsions. It can be seen from a direct comparison of emulsion 2 with comparison emulsion 8, or of emulsion 3 with comparison emulsion 9, that using the compounds according to the present invention as emulsifiers, a significantly lower emulsion viscosity is achieved: 6 compared with 36 and 10 compared with 52 Pas, which also, in contrast to the comparison emulsions, is stable over the storage period of at least 2 months, whereas in the case of comparison emulsion 8, the viscosity decreases significantly from 36 to 22 and in the case of comparison emulsion 9 from 52 to 28 Pas.

Emulsions 4 to 7 further show that the compounds according to the invention also lead to the desirably low emulsion viscosities in combination with conventional emulsifiers.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

The invention claimed is:

1. A dispersion or emulsion comprising at least one organopolysiloxane comprising, on average, at least one polyester group bounded to a siloxane via a spacer and, on average, at least one hydrophilic group bounded to the siloxane via a spacer, of general formula (I)

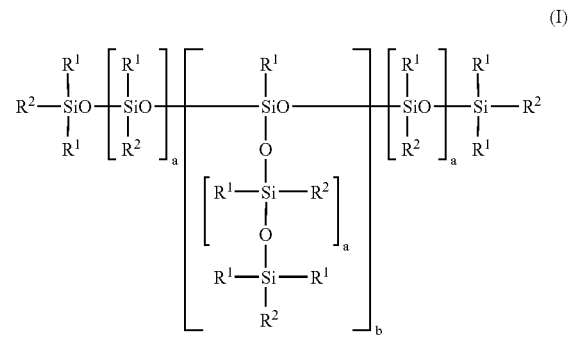

(I)

in which
  $R^1$ are identical or different and are alkyl radicals having 1 to 30 carbon atoms or phenyl radicals,
  $R^2$ independently of one another are $R^1$, -A-$R^3$ or —B—$R^4$ in which
    -A- is a divalent alkyleneoxy group having 3 to 24 carbon atoms, which is optionally branched and/or can contain double bonds, and/or is a divalent polyoxyalkylene group of the general average formula —$R^5$—$(C_2H_4O)_q$—$(C_3H_6O)_r$—$(C_4H_8O)_s$— in which
q=1 to 100,
r=0 to 100,
s=0 to 100,
R$^5$ is a divalent alkyleneoxy group having 1 to 24 carbon atoms, which is optionally branched and/or can contain double bonds,
R$^3$ is a polyester radical of the general formula

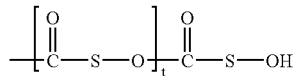

in which
t is an integer in the range from 2 to 5, and [—(O═C)—S—O—] is a radical of 12-hydroxystearic acid or of recinoleic acid;
—B— acts as a spacer between siloxane backbone and the radical R$^4$,
R$^4$ is a hydrophilic radical of the general average formula

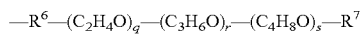

in which
q=1 to 100,
r=0 to 100,
s=0 to 100,
R$^6$ is a divalent alkylene or alkyleneoxy group having 1 to 24 carbon atoms which is optionally branched and/or can contain double bonds;
R$^7$ is a hydrogen atom, alkyl or acyl radical having 1 to 20 carbon atoms, or
R$^4$ is one of a polyhydroxyorganyl radical selected from the group consisting of glycerol and polyglycerol, a sugar or sugar derivative radical, a polyvinyl alcohol radical, a carboxylate, sulfate or phosphate radical, an ammonium radical or an amphoteric betaine or an amphoglycinate radical,
a has a value from 1 to 1000, and
b has a value from 0 to 10
with the proviso that, on statistical average, at least in each case one radical R$^2$=
A-R$^3$ and R$^2$=—B—R$^4$ is present, or in the case where no radical —B—R$^4$ is present, at least one radical R$^2$=-A-R$^3$ is present in which -A- is a divalent polyoxyalkylene group of the above-described general average formula

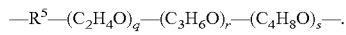

2. The dispersion or emulsion of claim 1 further comprising additional emulsifiers which when used in conjunction with the compound of general formula (I) provide a low-viscosity W/O emulsion having a high content of a dispersed phase.

3. The dispersion or emulsion of claim 1, wherein the hydrophilic radical R$^4$ is a radical selected from the group consisting of polyethers, polyglycerol, polyvinyl alcohol, sugar and sugar derivatives.

4. The dispersion or emulsion of claim 1, wherein b=0 and a=10 to 150.

5. A cosmetic W/O emulsion comprising 0.5 to 4% by weight, based on the total formulation, of at least one organopolysiloxane comprising, on average, at least one polyester group bounded to a siloxane via a spacer and, on average, at least one hydrophilic group bounded to the siloxane via a spacer, of general formula (I)

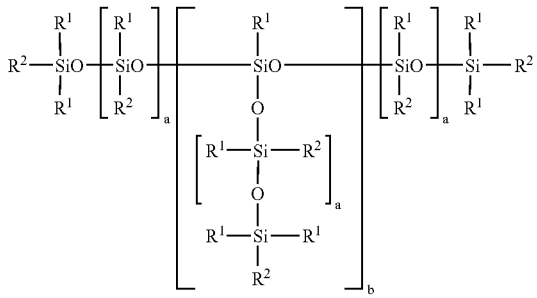

in which
R$^1$ are identical or different and are alkyl radicals having 1 to 30 carbon atoms or phenyl radicals,
R$^2$ independently of one another are R$^1$, -A-R$^3$ or —B—R$^4$
in which
-A- is a divalent alkyleneoxy group having 3 to 24 carbon atoms, which is optionally branched and/or can contain double bonds, and/or is a divalent polyoxyalkylene group of the general average formula

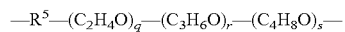

in which
q=1 to 100,
r=0 to 100,
s=0 to 100,
R$^5$ is a divalent alkyleneoxy group having 1 to 24 carbon atoms, which is optionally branched and/or can contain double bonds,
R$^3$ is a polyester radical of the general formula

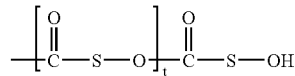

in which
t is an integer in the range from 2 to 5, and [—(O═C)—S—O—] is a radical of 12-hydroxystearic acid or of recinoleic acid;
—B— acts as a spacer between siloxane backbone and the radical R$^4$,
R$^4$ is a hydrophilic radical of the general average formula

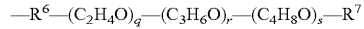

in which
q=1 to 100,
r=0 to 100,
s=0 to 100,
R$^6$ is a divalent alkylene or alkyleneoxy group having 1 to 24 carbon atoms which is optionally branched and/or can contain double bonds;
R$^7$ is a hydrogen atom, alkyl or acyl radical having 1 to 20 carbon atoms, or
R$^4$ is one of a polyhydroxyorganyl radical selected from the group consisting of glycerol and polyglycerol, a sugar or sugar derivative radical, a polyvinyl alcohol radical, a carboxylate, sulfate or phosphate radical, an ammonium radical or an amphoteric betaine or an amphoglycinate radical
a has a value from 1 to 1000, and
b has a value from 0 to 10
with the proviso that, on statistical average, at least in each case one radical R$^2$=

A-R³ and R²=—B—R⁴ is present, or in the case where no radical —B—R⁴ is present, at least one radical R²=-A-R³ is present in which -A- is a divalent polyoxyalkylene group of the above-described general average formula

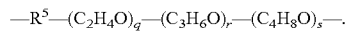

6. The cosmetic W/O emulsion of claim 5, wherein the hydrophilic radical R⁴ is a radical selected from the group consisting of polyethers, polyglycerol, polyvinyl alcohol, sugar and sugar derivatives.

7. The cosmetic W/O emulsion of claim 5, wherein b=0 and a=10 to 150.

* * * * *